(12) United States Patent
Matsuki et al.

(10) Patent No.: US 11,944,590 B2
(45) Date of Patent: Apr. 2, 2024

(54) CONTINUOUS MANUFACTURING SYSTEM AND METHOD

(71) Applicant: MITSUBISHI CHEMICAL ENGINEERING CORPORATION, Tokyo (JP)

(72) Inventors: Akihiro Matsuki, Tokyo (JP); Nobuhiro Tanaka, Tokyo (JP); Katsuhiro Murata, Tokyo (JP); Hironobu Takeda, Tokyo (JP)

(73) Assignee: MITSUBISHI CHEMICAL ENGINEERING CORPORATION, Tokyo (JP)

(*) Notice: Subject to any disclaimer, the term of this patent is extended or adjusted under 35 U.S.C. 154(b) by 892 days.

(21) Appl. No.: 16/975,094

(22) PCT Filed: Feb. 22, 2018

(86) PCT No.: PCT/JP2018/006513
§ 371 (c)(1),
(2) Date: Aug. 21, 2020

(87) PCT Pub. No.: WO2019/163059
PCT Pub. Date: Aug. 29, 2019

(65) Prior Publication Data
US 2020/0397658 A1 Dec. 24, 2020

(51) Int. Cl.
*B65G 53/56* (2006.01)
*A61J 3/10* (2006.01)
(Continued)

(52) U.S. Cl.
CPC ............... *A61J 3/10* (2013.01); *G01N 21/85* (2013.01); *G01N 33/15* (2013.01); *G01N 2021/8592* (2013.01)

(58) Field of Classification Search
CPC .................................................... B07C 5/363
See application file for complete search history.

(56) References Cited

U.S. PATENT DOCUMENTS 4,117,935 A 10/1978 Richardson et al.
4,193,502 A * 3/1980 Marmo ................. G21C 17/06
209/555
(Continued)

FOREIGN PATENT DOCUMENTS

DE 3929709 3/1991
EP 3816747 A1 * 5/2021 ....... G05B 19/41875
(Continued)

OTHER PUBLICATIONS

Extended European Search Report issued in corresponding EP application No. 18907262.2, dated Aug. 10, 2021.
(Continued)

*Primary Examiner* — Joseph A Dillon, Jr.
(74) *Attorney, Agent, or Firm* — Knobbe Martens Olson & Bear LLP (57) ABSTRACT

A continuous manufacturing system continuously manufactures a product from a powder of a raw material. The system includes a first processing device that performs first processing on the powder of the raw material; a second processing device that performs second processing on the powder on which the first processing device has performed the first processing; and an inspection and sorting device including an inspection chamber into which powder sent from the first processing device flows. When a prescribed amount of the powder has accumulated in the inspection chamber, the inspection and sorting device inspects the powder inside the inspection chamber after blocking a path connecting the first processing device to the inspection chamber. When the inspection ends, the inspection and (Continued)

sorting device removes the blocking after discharging the powder from inside the inspection chamber.

7 Claims, 5 Drawing Sheets

(51) Int. Cl.
  *G01N 21/85* (2006.01)
  *G01N 33/15* (2006.01)

(56) References Cited

U.S. PATENT DOCUMENTS

| | | | | |
|---|---|---|---|---|
| 4,222,488 | A * | 9/1980 | Jones | B07C 5/3412 |
| | | | | 209/583 |
| 4,570,783 | A * | 2/1986 | Newcom | B65G 47/5113 |
| | | | | 198/347.1 |
| 5,106,241 | A * | 4/1992 | Shinagawa | B65G 53/40 |
| | | | | 406/182 |
| 5,157,976 | A | 10/1992 | Tokoyama et al. | |
| 5,309,773 | A * | 5/1994 | Tokoyama | B04C 5/14 |
| | | | | 250/222.2 |
| 7,057,722 | B2 * | 6/2006 | Gehrlein | B30B 15/304 |
| | | | | 356/419 |
| 9,713,575 | B2 * | 7/2017 | Boeckx | A61J 3/10 |
| 10,189,054 | B2 * | 1/2019 | Fuchigami | G01N 33/15 |
| 10,947,064 | B2 * | 3/2021 | Tanaka | B65G 53/04 |
| 11,644,822 | B2 * | 5/2023 | Kawano | G05B 19/41875 |
| | | | | 700/95 |
| 11,675,343 | B2 * | 6/2023 | Kawano | G05B 19/41875 |
| | | | | 700/109 |
| 2003/0194281 | A1 * | 10/2003 | McKinnis | B07C 5/362 |
| | | | | 406/181 |
| 2012/0061869 | A1 | 3/2012 | Jurgen et al. | |
| 2016/0310365 | A1 | 10/2016 | Jurgen et al. | |
| 2018/0056332 | A1 | 3/2018 | Shouji et al. | |
| 2021/0263507 | A1 * | 8/2021 | Kawano | G05B 19/41875 |
| 2021/0278828 | A1 * | 9/2021 | Kawano | G05B 19/41875 |
| 2022/0072821 | A1 * | 3/2022 | Matsuki | B08B 5/02 |
| 2022/0258114 | A1 * | 8/2022 | Vanderputten | B01F 33/8051 |

FOREIGN PATENT DOCUMENTS

| | | | | |
|---|---|---|---|---|
| JP | | 11-267596 A | 10/1999 | |
| JP | | 2004-151029 | 5/2004 | |
| JP | | 2008-183168 A | 8/2008 | |
| JP | | 2012-525895 A | 10/2012 | |
| JP | | 5798400 B2 | 10/2015 | |
| JP | | 2018-034113 A | 3/2018 | |
| JP | | 7224166 B2 * | 2/2023 | B08B 5/02 |
| WO | WO 2009/130539 A1 | | 10/2009 | |
| WO | WO 2014/080322 | | 5/2014 | |

OTHER PUBLICATIONS

Shigemi Isobe, "Continuous manufacturing system for medicine (solid dosage forms)", Funtai Gijutsu, vol. 8, No. 12, pp. 1169-1173, Dec. 1, 2016.
Takeshi Terada, "Application of PAT tools on continuous manufacturing of solid dosage forms", Journal of Pharmaceutical Machinery and Engineering, vol. 25, No. 5, pp. 451-454, Dec. 22, 2016.
Freund Corporation, "Development of innovative continuous granulating apparatus "Granuformer" concept model", Chemical Apparatus, vol. 56, No. 7, pp. 2-3, Jul. 1, 2014.
International Search Report issued in application No. PCT/JP2018/006513, dated May 29, 2018.
Communication pursuant to Article 94(3) EPC, issued in EP Application No. 18907262.2, dated Aug. 2, 2023.

* cited by examiner

CONTINUOUS MANUFACTURING SYSTEM AND METHOD

TECHNICAL FIELD

The present invention relates to a continuous manufacturing system and method.

BACKGROUND ART

When producing medicines or food products, for example, various kinds of inspections are performed to ensure the quality of the product. For example, when producing a medicine in a tablet form, the moisture content of a granulate material produced using a granulator, a dryer, and the like is measured before the granulate is placed into a tablet press in order to ensure that the tablets will have a prescribed hardness (see PTL 1, for example).

DOCUMENTS OF PRIOR ARTS

Patent Document

[PTL 1] Japanese Patent No. 5798400

SUMMARY OF THE INVENTION

Problems to be Solved by the Invention

At production sites which handle powder raw materials, devices are prepared to handle different processes, such as mixing, granulation, and drying, and receptacles are used to move the raw materials (also including "intermediate products" hereinafter) between the respective processes. In this kind of production method, which is called a "batch type", inspections for ensuring the quality of the product are performed by extracting a sample from a receptacle containing a raw material. If the inspection result indicates a defect, the raw material in the receptacle from which the sample was taken is discarded, for example.

However, with the batch type, when a sample is determined to be defective, all the raw material in the receptacle from which the sample was extracted will also be determined to be defective and discarded, even when it is possible that non-defective raw material is present as well. It is desirable, therefore, to produce medicines, food products, and the like continuously, and automatically control parameters of the production process to ensure that no quality problems arise. To automatically control parameters of the production process suitably in the continuous production of medicines, food products, and the like, highly-accurate measurements of parameters pertaining to quality must be taken continuously. However, parameters such as hardness and solubility cannot be measured directly and continuously in a non-destructive manner. As such, for parameters such as hardness and solubility which cannot be measured directly and continuously in a non-destructive manner, a method is employed in which quality is managed indirectly using other parameters related to the aforementioned parameters, such as moisture or particle size distribution and lubricant content. If the parameters such as moisture or particle size distribution are measured through spectroanalysis, for example, it is very important to suppress disturbances which reduce the measurement accuracy, such as fluctuations in the bulk density of the powder to be measured. Additionally, in continuous production, when a quality problem has been detected from a measured parameter, it is necessary to quickly evacuate the problematic part during the production process before that part mixes with other parts.

Accordingly, an object of the present invention is to provide a continuous manufacturing system and method which can improve the reliability of parameters when handling a powder as a raw material in continuous production equipment.

Means for Solving the Problems

To achieve the above-described object, in the present invention, an inspection and sorting device is provided between a first processing device and a second processing device in a continuous manufacturing system that continuously manufactures a product from a powder of a raw material, the inspection and sorting device having an inspection chamber into which powder sent from the first processing device flows. When a prescribed amount of the powder has accumulated in the inspection chamber, the powder inside the inspection chamber is inspected after blocking a path connecting the first processing device to the inspection chamber, and when the inspection ends, the blocking is removed after discharging the powder from inside the inspection chamber.

Specifically, a continuous manufacturing system according to the present invention is a system that continuously manufactures a product from a powder of a raw material, the system including: a first processing device that performs first processing on the powder of the raw material; a second processing device that performs second processing on the powder on which the first processing device has performed the first processing; and an inspection and sorting device including an inspection chamber into which powder sent from the first processing device flows, wherein when a prescribed amount of the powder has accumulated in the inspection chamber, the inspection and sorting device inspects the powder inside the inspection chamber after blocking a path connecting the first processing device to the inspection chamber, and when the inspection ends, the inspection and sorting device removes the blocking after discharging the powder from inside the inspection chamber.

In the above-described continuous manufacturing system, when a prescribed amount of the powder has accumulated in the inspection chamber, which is provided between the first processing device and the second processing device in the continuous manufacturing system that continuously manufactures a product from a powder of a raw material, and into which the powder sent from the first processing device flows, the powder inside the inspection chamber is inspected after blocking the path connecting the first processing device to the inspection chamber. Accordingly, the inspection of the powder inside the inspection chamber is performed with a bulk density of the raw material in a constant state each time. There is also almost no chance of measurement values of the inspection varying depending on the bulk density of the powder. Accordingly, in the continuous manufacturing system that continuously manufactures a product from a powder raw material, variations in measurement values caused by the bulk density of the powder changing from inspection to inspection can be suppressed, and the measurement values can be obtained accurately.

Note that the inspection and sorting device may include an entry-side sluice valve that opens and closes a path connecting the first processing device to the inspection chamber; when the prescribed amount of the powder has accumulated in the inspection chamber, the inspection and sorting device may inspect the powder inside the inspection chamber after closing the entry-side sluice valve; and when the inspection of the powder inside the inspection chamber ends, the inspection and sorting device may open the entry-side sluice valve after discharging the powder from inside the inspection chamber. According to the continuous manufacturing system having this inspection and sorting device, raw material which, during the inspection, has been sent from the first processing device to the inspection and sorting device and accumulated on an upstream side of the entry-side sluice valve enters the inspection chamber when the entry-side sluice valve is opened, and thus that raw material can be fully inspected as well.

Note that the inspection and sorting device may include an exit-side sluice valve that is provided in a bottom part of the inspection chamber and that opens and closes a discharge path of the inspection chamber; when the prescribed amount of the powder has accumulated in the inspection chamber with the exit-side sluice valve in a closed state, the inspection and sorting device may inspect the powder inside the inspection chamber after blocking the path connecting the first processing device to the inspection chamber; and when the inspection ends, the inspection and sorting device may remove the blocking after opening the exit-side sluice valve and discharging the powder from inside the inspection chamber. According to the continuous manufacturing system having this inspection and sorting device, the raw material inside the inspection chamber is supported from below by the exit-side sluice valve, and thus the raw material can be inspected in a stable manner.

Additionally, the inspection and sorting device may include path changeover means for changing a discharge path from the inspection chamber between a path connecting the inspection chamber to the second processing device, and a path connecting the inspection chamber to a destination aside from the second processing device; and when the inspection ends, the inspection and sorting device may remove the blocking after changing the discharge path in accordance with a result of the inspection using the path changeover means and discharging the powder from inside the inspection chamber. According to the continuous manufacturing system having this inspection and sorting device, when, for example, an inspection result indicates a defect, the defective raw material can be prevented from being sent to the second processing device.

Additionally, the inspection and sorting device may include a sensor that senses whether or not the powder that has accumulated in the inspection chamber has reached a prescribed height, and the inspection and sorting device may perform the inspection when the sensor senses that the prescribed amount of the powder has accumulated in the inspection chamber. According to the continuous manufacturing system having this inspection and sorting device, the powder can be accumulated inside the inspection chamber to a constant height.

Additionally, the first processing device may adjust an operation amount in accordance with a result of the inspection. For example, when the first processing device is a dryer that dries the powder of the raw material and the second processing device is a mixer that mixes the powder of the raw material, a moisture amount in the raw material can be controlled by adjusting a temperature, an air flow amount, and so on of the dryer in accordance with the result of the inspection.

Note that the present invention can be realized as a method aspect as well. For example, the present invention may be a continuous manufacturing method of continuously manufacturing a product from a powder of a raw material, the method being executed in an inspection and sorting device which is provided in a path between a first processing device that performs first processing on the powder of the raw material and a second processing device that performs second processing on the powder on which the first processing device has performed the first processing, and which includes an inspection chamber into which powder sent from the first processing device flows, the method including: when a prescribed amount of the powder has accumulated in the inspection chamber, inspecting the powder inside the inspection chamber after blocking a path connecting the first processing device to the inspection chamber; and when the inspection ends, removing the blocking after discharging the powder from inside the inspection chamber.

Effects of the Invention

According to the above-described continuous manufacturing system and method, the reliability of parameters when handling a powder as a raw material in continuous production equipment can be improved.

DETAILED DESCRIPTION OF THE PREFERRED EMBODIMENT

An embodiment will be described hereinafter. The embodiment described hereinafter is merely an example, and the technical scope of the present disclosure is not intended to be limited to the following embodiment.

<Hardware Configuration>

Figure 1:
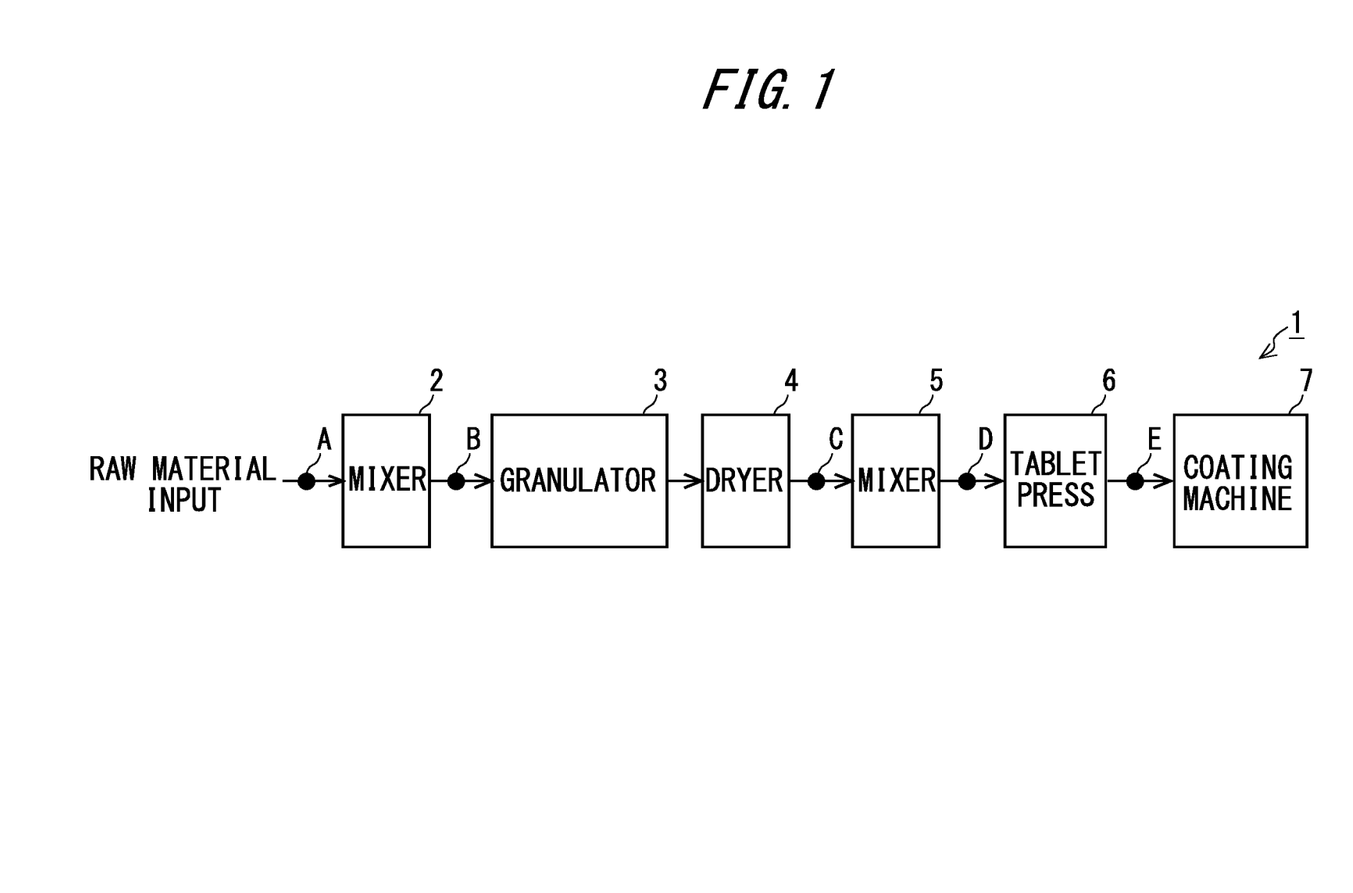
FIG. 1 is a diagram illustrating a continuous manufacturing system according to an embodiment.

FIG. 1 is a diagram illustrating a continuous manufacturing system 1 according to the embodiment. Although the present embodiment will describe producing a medicine as an example, the present embodiment can also be applied in the production of food products and other types of products, for example. The continuous manufacturing system 1 is a system that produces tablets from a powder raw material, and as illustrated in FIG. 1, includes a mixer 2, a granulator 3, a dryer 4, a mixer 5, a tablet press 6, and a coating machine 7. The mixer 2 includes an input port into which the powder raw material is input, and mixes various types of powders, liquids, and the like serving as the raw materials for the tablets. The granulator 3 granulates the raw materials mixed by the mixer 2 by causing those raw materials to bind together into small particle groups. The dryer 4 adds various types of additional raw materials to the raw materials granulated by the granulator 3 and dries the raw materials. The mixer 5 mixes the granular raw materials dried by the dryer 4. The tablet press 6 creates tablets from the granular raw materials mixed by the mixer 5 by pressurizing those raw materials in a mold. The coating machine 7 applies a coating to the tablets solidified by the tablet press 6. In the continuous manufacturing system 1, the series of equipment, from the mixer 2 to the coating machine 7, are connected. Accordingly, with the continuous manufacturing system 1, a variety of processes performed by each piece of equipment in the series from the mixer 2 to the coating machine 7 can be performed continuously on the raw materials input to the mixer 2.

Although FIG. 1 illustrates one each of the devices in the series from the mixer 2 to the coating machine 7, the continuous manufacturing system 1 is not limited to this form. For example, one or more of the mixer 2, the granulator 3, and the dryer 4 may be prepared, and a plurality of types of raw materials may be mixed in the mixer 5.

The series of equipment from the mixer 2 to the coating machine 7 is controlled by a control device (not shown) provided in the continuous manufacturing system 1. The control device determines an operation amount for each device on the basis of measurement values from various types of sensors provided in the continuous manufacturing system 1. For example, values obtained from the various devices among the mixer 2 to the coating machine 7, such as a rotational speed of a screw feeder provided in the mixer 2 and a temperature of the dryer 4, as well as values obtained from sensors provided partway along paths connecting the devices, are included as the measurement values to which the control device refers. Positions such as those indicated by the letters A to E in FIG. 1 can be given as examples of the positions where the sensors are provided partway along the paths connecting the devices. If a sensor is installed at the letter C, which is partway along the path connecting the dryer 4 and the mixer 5, the control device can change operation amounts of the granulator 3, the mixer 5, and so on in accordance with the properties of the raw material which has exited the dryer 4, for example. Additionally, if a sensor is installed at the letter B, which is partway along the path connecting the mixer 2 and the granulator 3, the control device can change the destination of the raw material which has exited the mixer 2 to a destination aside from the granulator 3 in accordance with the properties of that raw material, for example.

Figure 2:
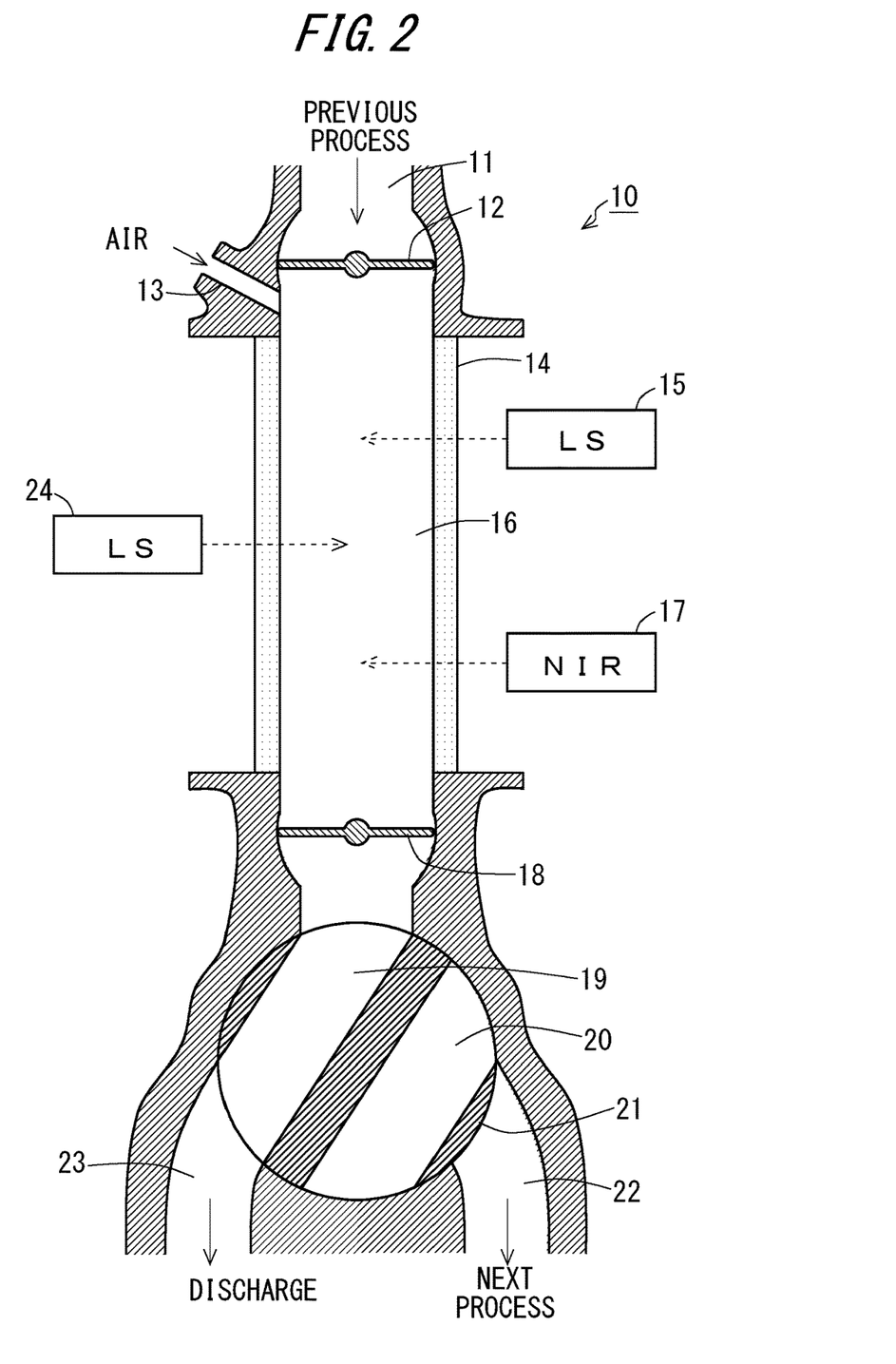
FIG. 2 is a diagram illustrating an example of an inspection and sorting device provided in the continuous manufacturing system.

FIG. 2 is a diagram illustrating an example of an inspection and sorting device 10 provided in the continuous manufacturing system 1. The inspection and sorting device can be provided at any suitable location in the continuous manufacturing system 1. The inspection and sorting device 10 is provided partway along the paths connecting the various devices, from the mixer 2 to the coating machine 7, as indicated by the letters A to E in FIG. 1, for example.

The inspection and sorting device 10 includes: an inflow path 11 into which a raw material sent from a device connected to an upstream side of the inspection and sorting device 10 flows; an entry-side sluice valve 12 provided on a lower end of the inflow path 11; an inspection chamber 16 formed below the entry-side sluice valve 12; an air blowing channel 13 provided near the entry-side sluice valve 12; a sight glass 14 which constitutes a wall surface of the inspection chamber 16 and enables the inside of the inspection chamber 16 to be seen from the periphery; and an exit-side sluice valve 18 provided at a lower part of the sight glass 14. Laser sensors 15 and 24 and a spectral analyzer 17, which take optical measurements of the inside of the inspection chamber 16 through the sight glass 14, are provided in the periphery of the inspection chamber 16. In the inspection and sorting device 10, when a raw material is sent from the device connected to the upstream side of the inspection and sorting device 10 while the entry-side sluice valve 12 is in an open state and the exit-side sluice valve 18 is in a closed state, that raw material accumulates in the inspection chamber 16. Once the laser sensor 15 senses that a prescribed amount of the raw material has accumulated in the inspection chamber 16, the entry-side sluice valve 12 closes, and the raw material is inspected using the spectral analyzer 17. A path changeover valve 21 (an example of "path changeover means" according to the present application) having valve holes 19 and 20 is provided below the exit-side sluice valve 18, and the inspected raw material is sent to an outflow path 22 or an outflow path 23 depending on the inspection result. Whether or not there is any raw material remaining in the inspection chamber 16 is then inspected by the laser sensor 24. Although the present embodiment describes an example in which a near-infrared sensor is used as the spectral analyzer 17, it should be noted that the continuous manufacturing system disclosed in the present application is not limited thereto. Additionally, although the present embodiment describes a so-called "diverter valve" as an example of the path changeover valve 21, the continuous manufacturing system disclosed in the present application is not limited thereto, and a path changeover mechanism using a different system may be used instead.

Figure 3A:
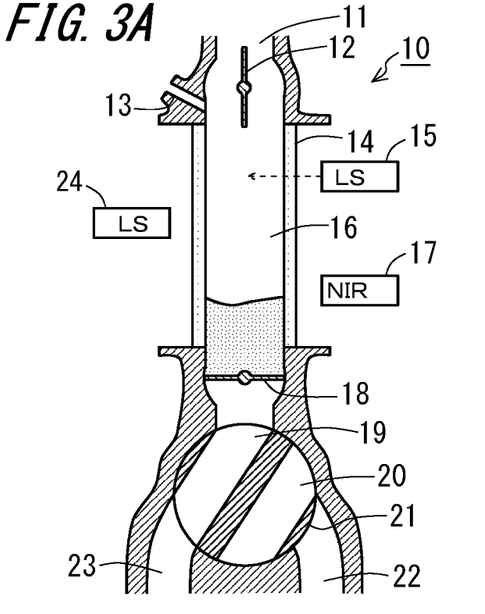
FIG. 3a is a first diagram illustrating operations of the inspection and sorting device.
Figure 3B:
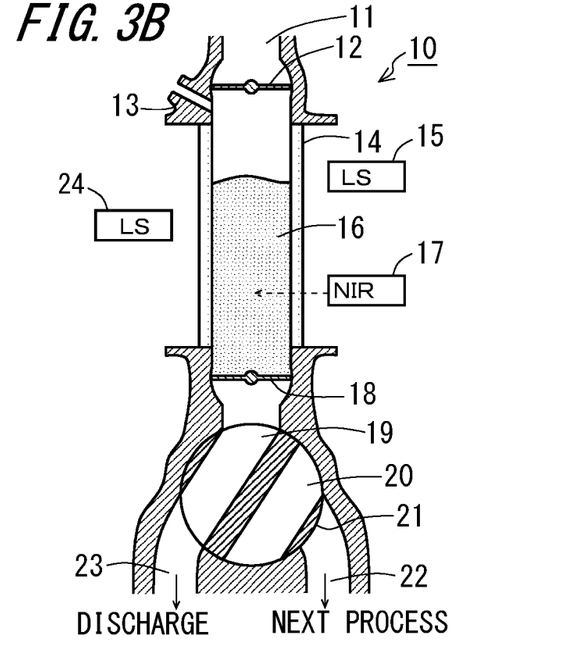
FIG. 3b is a second diagram illustrating operations of the inspection and sorting device.

FIG. 3a-3d is a diagram illustrating operations of the inspection and sorting device 10. The inspection and sorting device 10 is connected to the control device of the continuous manufacturing system 1. The inspection and sorting device 10 operates in the following manner in accordance with control signals sent from the control device of the continuous manufacturing system 1. That is, in the inspection and sorting device 10, when a raw material is sent from the device connected to the upstream side of the inspection and sorting device 10 while the entry-side sluice valve 12 is in an open state and the exit-side sluice valve 18 is in a closed state, that raw material accumulates inside the inspection chamber 16, as illustrated in FIG. 3A. Then, when the laser sensor 15 has sensed that the raw material accumulating inside the inspection chamber 16 has reached a prescribed height, the entry-side sluice valve 12 closes, as illustrated in FIG. 3B. Once the entry-side sluice valve 12 closes, the flow of new raw material from the inflow path 11 into the inspection chamber 16 stops. The bulk density of the raw material inside the inspection chamber 16 is kept constant while the flow of new raw material from the inflow path 11 into the inspection chamber 16 is stopped. Accordingly, the inspection of the raw material inside the inspection chamber 16 using the spectral analyzer 17 is started after the entry-side sluice valve 12 has been closed. Performing the inspection using the spectral analyzer 17 with the entry-side sluice valve 12 in a closed state ensures that no changes will arise in the bulk density of the raw material due to an increase in the height of the raw material accumulating inside the inspection chamber 16, and thus stable inspection results can be obtained.

Figure 3C:
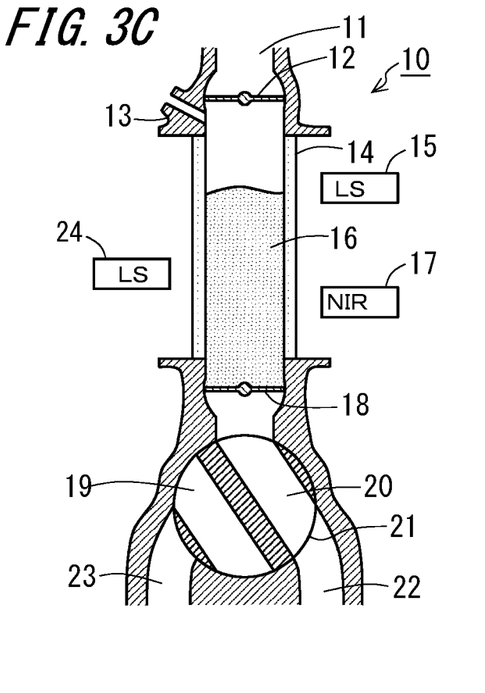
FIG. 3c is a third diagram illustrating operations of the inspection and sorting device.
Figure 3D:
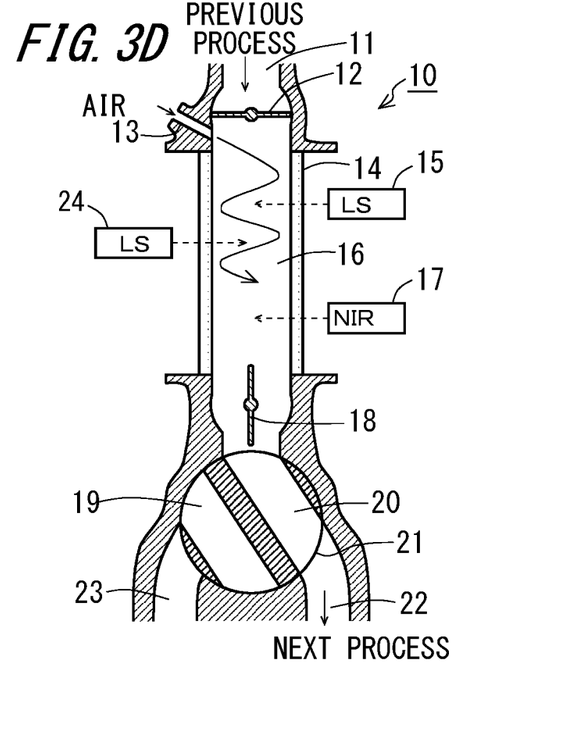
FIG. 3d is a fourth diagram illustrating operations of the inspection and sorting device.

After the inspection of the raw material accumulated inside the inspection chamber 16 is complete, an operation for changing over the path changeover valve 21 is performed in accordance with the inspection result. If, for example, the inspection result of the raw material accumulated inside the inspection chamber 16 indicates no defects, the direction of the path changeover valve 21 changes so that the outflow path 22, which is connected to the device which handles the next process to be performed on the raw material accumulated inside the inspection chamber 16, communicates with the valve hole 20, as illustrated in FIG. 3C. On the other hand, if, for example, the inspection result of the raw material accumulated inside the inspection chamber 16 indicates a defect, the direction of the path changeover valve 21 changes so that the outflow path 23, which is for discarding the raw material accumulated inside the inspection chamber 16, communicates with the valve hole 19. After the changeover operation by the path changeover valve 21 is complete, the exit-side sluice valve 18 opens, and at the same time as, or a set amount of time after, the exit-side sluice valve 18 opening, air begins being blown into the inspection chamber 16 from the air blowing channel 13, which quickly discharges the raw material which was inside the inspection chamber 16 from the interior of the inspection chamber 16, as illustrated in FIG. 3D. After the discharge of the raw material is complete, the blowing of air into the inspection chamber 16 from the air blowing channel 13 is stopped, and at the same time, the exit-side sluice valve 18 is closed; an optical inspection for remaining raw material is performed using the laser sensor 24, and the entry-side sluice valve 12 is opened again after the effect of the cleaning has been confirmed. When the entry-side sluice valve 12 opens, raw material which had been sent from the device on the upstream side of the inspection and sorting device 10 and which had accumulated above the entry-side sluice valve 12 while the entry-side sluice valve 12 was closed, flows into the inspection chamber 16.

The inspection and sorting device 10 performs the series of operations described with reference to FIGS. 3(A) to 3(D) repeatedly, every several tens of seconds to every several minutes. Accordingly, there is almost no chance that the inspection and sorting device 10 will pose a substantial obstruction to the continuous operations of the devices connected on the upstream side and the downstream side thereof. Furthermore, the inspection of the raw material using the spectral analyzer 17 is performed with the raw material at a prescribed height sensed by the laser sensor 15 and with the entry-side sluice valve 12 in a closed state, and thus the inspection is performed with the bulk density of the raw material in a constant state each time. As such, there is also almost no chance of the measurement values of the spectral analyzer 17 varying depending on the bulk density of the powder. Accordingly, with an inspection that uses the inspection and sorting device 10, measurement values which vary depending on the bulk density of a powder can be obtained accurately even in the continuous manufacturing system 1, which continuously produces tablets from a powder raw material. Furthermore, with the inspection and sorting device 10, all of the raw materials handled continuously by the continuous manufacturing system 1 can be inspected by the inspection chamber 16 and sorted by the path changeover valve 21, and thus even if a defective product has arisen in the continuous manufacturing system 1 temporarily, non-defective and defective products can be separated in units equivalent to the amount which accumulates inside the inspection chamber 16, making it possible to reduce discarded raw materials to the greatest extent possible.

An example of an overall control flow which can be implemented by the continuous manufacturing system 1 when the inspection and sorting device 10 is provided at the location indicated by the letter C in FIG. 1 will be described below.

The dryer 4 of the continuous manufacturing system 1 illustrated in FIG. 1 adds various types of additional raw materials to the raw material granulated by the granulator 3 and dries the raw materials. The dryer 4 is provided with at least one heater for heat-based drying, and the amount by which the heater is electrified is adjusted by the control device to achieve an appropriate drying temperature. The dryer 4 is also provided with a variable-speed blower, and a rotational speed of the blower is adjusted by the control device so that the raw material granulated by the granulator 3 travels through the dryer 4 at an appropriate speed.

Figure 4:
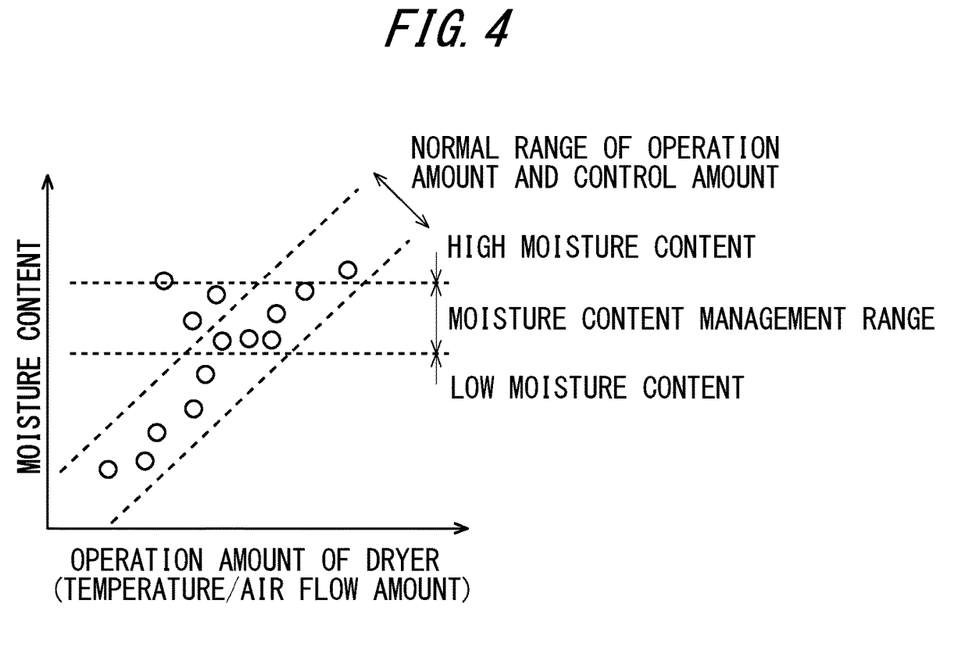
FIG. 4 is a graph illustrating an example of a correlation relationship between a moisture content of a raw material at an outlet port of a dryer and an operation amount of a dryer.

FIG. 4 is a graph illustrating an example of a correlation relationship between a moisture content of a raw material at an outlet port of the dryer 4 and an operation amount of the dryer 4. When, for example, the moisture content is relatively high, it is necessary to set the temperature of the dryer 4 higher, in accordance with that moisture content, in order to facilitate the drying. On the other hand, when the moisture content is relatively low, it is necessary to set the temperature of the dryer 4 lower, in accordance with that moisture content, in order to prevent overdrying. Accordingly, the temperature, air flow amount, and so on of the dryer 4 are adjusted by performing feedback control on operation amounts of the heater, the blower, and so on in accordance with the moisture content of the raw material which has exited the dryer 4. If the feedback control is performed correctly, the moisture content of the raw material which has exited the dryer 4 will fall within a stipulated management range. However, if the feedback control is not performed correctly, the moisture content of the raw material which has exited the dryer 4 will deviate from the stipulated management range. There are furthermore cases where the moisture content of the raw material which has exited the dryer 4 appears to be within the stipulated management range despite the operation amount deviating from a normal range due to some kind of problem in the moisture content measurement, a process, or the like. As illustrated in FIG. 4, such problems and the like in the moisture content measurement can be detected if normal ranges are set for the operation amount and the control amount beforehand.

In the continuous production of a medicine which uses a powder as a raw material, it is generally difficult to continuously measure the moisture content of the powder. However, with the inspection and sorting device 10 described above, the stated series of operations described with reference to FIGS. 3(A) to 3(D) is performed repeatedly, every several minutes, and thus even if the inspection and sorting device 10 is provided partway along the path connecting the dryer 4 and the mixer 5, there is almost no chance that doing so will pose a substantial obstruction to the continuous operations of the dryer 4 connected on the upstream side, the mixer 5 connected on the downstream side, and so on. Furthermore, the inspection of a moisture amount of the raw material using the spectral analyzer 17 is performed with the raw material at a prescribed height sensed by the laser sensor 15 and with the entry-side sluice valve 12 in a closed state, and thus there is almost no chance that measurement values for the moisture amount will vary due to variations in the bulk density of the raw material. As such, if, in the continuous manufacturing system 1 according to the present embodiment, the above-described inspection and sorting device 10 is provided partway along the path connecting the dryer 4 and the mixer 5, feedback control can be performed on the temperature, air flow amount, and so on of the dryer 4 on the basis of the moisture content in the raw material which has exited the dryer 4. If a particle size measurement device is also provided in the inspection and sorting device 10, feedback control will also be possible for, for example, an operation amount of the granulator 3 located on the upstream side of the dryer 4 (e.g., a granulation rotation speed or the like).

Figure 5:
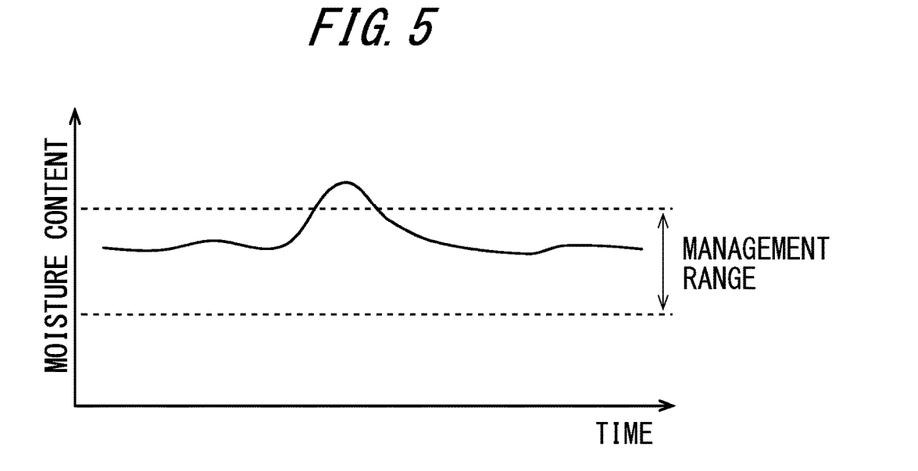
FIG. 5 is a graph illustrating an example of changes over time in a moisture content of a raw material which has exited the dryer.

Additionally, the inspection and sorting device 10 is provided with the path changeover valve 21, and thus if, in the continuous manufacturing system 1 according to the present embodiment, the above-described inspection and sorting device 10 is provided partway along the path connecting the dryer 4 and the mixer 5, the raw material which is processed continuously can be discharged in accordance with the inspection result. FIG. 5 is a graph illustrating an example of changes over time in the moisture content of a raw material which has exited the dryer 4. For example, as illustrated in FIG. 5, it is possible that the moisture content of the raw material which has exited the dryer 4 will temporarily deviate from the management range. In such a case, it is undesirable for the raw material, which has a moisture content deviating from the management range, to be sent to the mixer 5. However, the inspection and sorting device 10 is provided with the path changeover valve 21, and thus if the above-described inspection and sorting device 10 is provided partway along the path connecting the dryer 4 and the mixer 5, a raw material which has a moisture content deviating from the management range in the inspection of the inspection chamber 16 can be discharged by the path changeover valve 21 to a location aside from the mixer 5.

Figure 6:
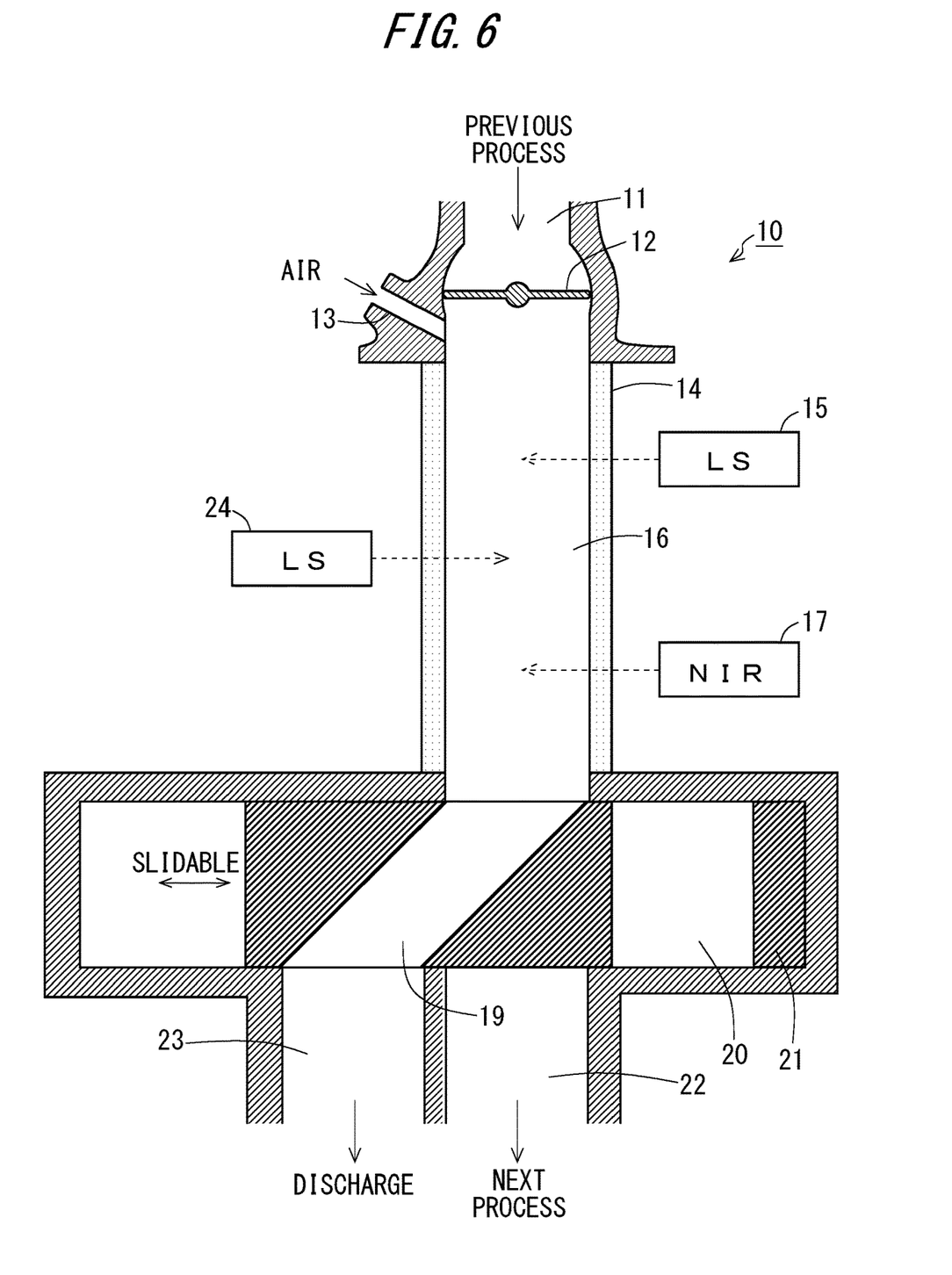
FIG. 6 is a diagram illustrating a variation on the inspection and sorting device.

FIG. 6 is a diagram illustrating a variation on the inspection and sorting device 10. As illustrated in FIG. 6, the path changeover valve 21 of the inspection and sorting device 10 may have a plate-shaped valve body which slides to the left and right, which enables one of the outflow path 22 and the outflow path 23 to communicate with the inspection chamber 16. The path changeover valve 21 of the inspection and sorting device 10 may, for example, change the flow path over using a disk-shaped valve body, or may change the flow path over using a plate-shaped valve body.

DESCRIPTION OF THE REFERENCE NUMERALS AND SYMBOLS

1 Continuous manufacturing system
2 Mixer
3 Granulator
4 Dryer
5 Mixer
6 Tablet press
7 Coating machine
10 Inspection and sorting device
11 Inflow path
12 Entry-side sluice valve
13 Air blowing channel
14 Sight glass
15, 24 Laser sensor
16 Inspection chamber
17 Spectral analyzer
18 Exit-side sluice valve
19, 20 Valve hole
21 Path changeover valve
22, 23 Outflow path

What is claimed is:

1. A continuous manufacturing system that continuously manufactures a product from a powder of a raw material, the system comprising:
a first processing device that performs first processing on the powder of the raw material;
a second processing device that performs second processing on the powder on which the first processing device has performed the first processing; and
an inspection and sorting device including an inspection chamber into which powder sent from the first processing device flows, wherein
when a prescribed amount of the powder has accumulated in the inspection chamber, the inspection and sorting device inspects the powder inside the inspection chamber after blocking a path connecting the first processing device to the inspection chamber;
when the inspection ends, the inspection and sorting device removes the blocking after discharging the powder from inside the inspection chamber; and
the inspection and sorting device includes a sensor that senses whether or not the powder that has accumulated in the inspection chamber has reached a prescribed height, and the inspection and sorting device performs the inspection when the sensor senses that the prescribed amount of the powder has accumulated in the inspection chamber.

2. The continuous manufacturing system according to claim 1, wherein
the inspection and sorting device includes an entry-side sluice valve that opens and closes a path connecting the first processing device to the inspection chamber;
when the prescribed amount of the powder has accumulated in the inspection chamber, the inspection and sorting device inspects the powder inside the inspection chamber after closing the entry-side sluice valve; and
when the inspection of the powder inside the inspection chamber ends, the inspection and sorting device opens the entry-side sluice valve after discharging the powder from inside the inspection chamber.

3. The continuous manufacturing system according to claim 1, wherein
the inspection and sorting device includes an exit-side sluice valve that is provided in a bottom part of the inspection chamber and that opens and closes a discharge path of the inspection chamber;
when the prescribed amount of the powder has accumulated in the inspection chamber with the exit-side sluice valve in a closed state, the inspection and sorting device inspects the powder inside the inspection chamber after blocking the path connecting the first processing device to the inspection chamber; and
when the inspection ends, the inspection and sorting device removes the blocking after opening the exit-side sluice valve and discharging the powder from inside the inspection chamber.

4. The continuous manufacturing system according to claim 1, wherein
the inspection and sorting device includes path changeover means for changing a discharge path from the inspection chamber between a path connecting the inspection chamber to the second processing device, and a path connecting the inspection chamber to a destination aside from the second processing device; and
when the inspection ends, the inspection and sorting device removes the blocking after changing the discharge path in accordance with a result of the inspection using the path changeover means and discharging the powder from inside the inspection chamber.

5. The continuous manufacturing system according to claim 1, wherein
the first processing device adjusts an operation amount in accordance with a result of the inspection.

6. The continuous manufacturing system according to claim 1, wherein
the first processing device is a dryer that dries the powder of the raw material; and
the second processing device is a mixer that mixes the powder of the raw material.

7. A continuous manufacturing method of continuously manufacturing a product from a powder of a raw material, the method being executed in an inspection and sorting device which is provided in a path between a first processing device that performs first processing on the powder of the raw material and a second processing device that performs second processing on the powder on which the first processing device has performed the first processing, and which includes an inspection chamber into which powder sent from the first processing device flows, the method comprising:

when a prescribed amount of the powder has accumulated in the inspection chamber, inspecting the powder inside the inspection chamber after blocking a path connecting the first processing device to the inspection chamber;

when the inspection ends, removing the blocking after discharging the powder from inside the inspection chamber; and the inspection and sorting device includes a sensor that senses whether or not the powder that has accumulated in the inspection chamber has reached a prescribed height, and the inspection and sorting device performs the inspection when the sensor senses that the prescribed amount of the powder has accumulated in the inspection chamber.

* * * * *